United States Patent [19]
Fischer et al.

[11] Patent Number: 6,083,489
[45] Date of Patent: Jul. 4, 2000

[54] DENTIFRICES INCORPORATING SPHERICAL PARTICLES FOR ENHANCED CLEANING OF TEETH

[75] Inventors: Dan E. Fischer, Sandy; Steven D. Jensen, South Jordan, both of Utah

[73] Assignee: Ultradent Products, Inc., South Jordan, Utah

[21] Appl. No.: 09/360,720

[22] Filed: Jul. 27, 1999

Related U.S. Application Data

[63] Continuation-in-part of application No. 09/181,103, Oct. 28, 1998, Pat. No. 6,010,683, which is a continuation-in-part of application No. 08/964,502, Nov. 5, 1997, abandoned.

[51] Int. Cl.⁷ .................. A61K 7/16; A61K 7/18
[52] U.S. Cl. ................................. 424/52; 424/49
[58] Field of Search ......................... 424/49–88

[56] References Cited

U.S. PATENT DOCUMENTS

| | | | |
|---|---|---|---|
| Re. 29,808 | 10/1978 | Wagner | 51/401 |
| 2,196,154 | 4/1940 | Schulerud | 167/93 |
| 2,806,772 | 9/1957 | Robie | 51/296 |
| 2,986,455 | 5/1961 | Sandmeyer | 51/296 |
| 2,995,521 | 8/1961 | Etignard-Bluard | 252/90 |
| 3,715,604 | 2/1973 | Colodney et al. | 424/52 |
| 3,803,301 | 4/1974 | Cordon et al. | 424/49 |
| 3,929,987 | 12/1975 | Colodney et al. | 424/52 |
| 3,946,108 | 3/1976 | Tomlinson et al. | 424/49 |
| 3,947,567 | 3/1976 | Berg, Jr. et al. | 424/45 |
| 3,955,942 | 5/1976 | Cordon et al. | 51/295 |
| 3,985,668 | 10/1976 | Hartman | 252/99 |
| 3,988,433 | 10/1976 | Benedict | 424/53 |
| 4,051,056 | 9/1977 | Hartman | 252/99 |
| 4,066,745 | 1/1978 | Tomlinson et al. | 424/49 |
| 4,102,992 | 7/1978 | Davis | 424/49 |
| 4,111,713 | 9/1978 | Beck | 106/288 |
| 4,132,533 | 1/1979 | Lohmer et al. | 51/295 |
| 4,543,106 | 9/1985 | Pargkh | 51/295 |
| 4,588,582 | 5/1986 | Motarjemi | 424/49 |
| 4,770,634 | 9/1988 | Pellico | 433/217.1 |
| 4,799,939 | 1/1989 | Bloecher et al. | 51/293 |
| 4,834,969 | 5/1989 | Grollier | 424/49 |
| 5,037,453 | 8/1991 | Narayanan et al. | 51/307 |
| 5,071,637 | 12/1991 | Pellico | 424/45 |
| 5,073,363 | 12/1991 | Pellico | 424/49 |
| 5,124,143 | 6/1992 | Müllemann et al. | 424/49 |
| 5,266,304 | 11/1993 | Baffelli et al. | 424/49 |
| 5,443,603 | 8/1995 | Kirkendall | 51/296 |
| 5,472,461 | 12/1995 | Li | 51/296 |
| 5,597,553 | 1/1997 | Baffelli et al. | 424/49 |
| 5,824,289 | 10/1998 | Stoltz | 424/45 |

FOREIGN PATENT DOCUMENTS

| 1319875 | 7/1993 | Canada | 134/44 |
|---|---|---|---|
| WO82/03975 | 11/1982 | WIPO . | |

*Primary Examiner*—Shep K. Rose
*Attorney, Agent, or Firm*—Workman, Nydegger & Seeley

[57] ABSTRACT

Toothpaste and other dentifrices formulated to include substantially spherical cleaning particles for enhanced plaque-removal capability. The cleaning particles are relatively large, having a diameter in a range from about 10 microns to about 200 microns, and are substantially round-edge and nonjagged so as to be far less abrasive compared to conventional abrasive particles, which tend to have a more jagged profile. Preferred cleaning particles include hollow glass spheres, which not only provide enhanced plaque-removal properties but which yield dental compositions having greatly reduced density. Air and other gases may optionally be entrained into the inventive dental compositions, either during manufacture or upon dispensing the dental compositions onto a toothbrush.

13 Claims, No Drawings

DENTIFRICES INCORPORATING SPHERICAL PARTICLES FOR ENHANCED CLEANING OF TEETH

BACKGROUND OF THE INVENTION

1. Related Applications

This application is a continuation-in-part of U.S. application Ser. No. 09/181,103, filed Oct. 28, 1998, now U.S. Pat. No. 6,010,683 which is a continuation-in-part of U.S. application Ser. No. 08/964,502, filed Nov. 5, 1997 (abandoned). For purposes of disclosure, the foregoing applications are incorporated herein by specific reference.

2. The Field of the Invention

The present invention is in the field of oral dentifrices, particularly in the field of toothpastes. More particularly, the present invention relates to toothpastes and other dentifrices that include round-edged cleaning particles of relatively large size in addition to, or instead of, conventional abrasives. Larger, more spherical cleaning particles are far less abrasive but have greatly enhanced plaque-removal power compared to conventional abrasives and polishes used in toothpastes.

3. The Relevant Technology

Toothpastes and other dentifrices are widely used in America and throughout the world to provide good oral hygiene, to prevent tooth decay, remove stains and to treat or minimize other problems associated with oral hygiene, such as gum disease and foul breath odor. Toothpastes typically include an inert carrier gel or paste, abrasive agents for removing stains, plaque and other foreign materials found on a person's teeth, decay prevention medicaments, such as fluorides, flavorants, surfactants, detergents, and other additives to provide a desired consistency and cleansing or medicinal activity.

Fluoride has been medically proven to aid in the prevention of tooth decay. Typically, tooth decay causing agents generally comprise acids formed by bacterial breakdown of sugars in a person's mouth. Enamel treated with fluoride is much more resistant to such acidic attack compared to enamel that has not been treated with fluoride. Nevertheless, even teeth that have been treated with fluoride are subject to attack and decay, particularly if the teeth are not cleaned on a regular basis. One of the major causes of tooth decay is the inability to adequately remove the plaque layer which tends to build up on the tooth surfaces over time, particularly after eating.

Plaque is defined as a soft layer or deposit of bacteria and bacteria products which builds up on the teeth. Because it consists in large part of bacteria which secrete cavity-forming acids, it is a major contributor or factor in the formation of cavities. Because plaque is ubiquitously and continuously formed on teeth, tooth enamel is potentially under constant attack to the extent that plaque is not adequately removed on a frequent basis.

Plaque and other foreign substances that build up on teeth, such as tarter, can be entirely or nearly entirely removed by a dentist or dental hygienist during routine cleaning using prophylaxis paste and by scraping and other techniques. However, because people visit their dentists only infrequently, such visits cannot be relied up to entirely prevent cavities. Daily brushing is an integral part of good dental hygiene and cavity-prevention.

While brushing using conventional toothpastes can and does remove substantial amounts of plaque, such toothpastes are often inadequate in removing all or virtually all of the plaque, particularly when the person using such toothpastes chooses not to brush for more than short periods of time. On the other hand, while a longer brushing routine will tend to remove more plaque compared to shorter brushing routines, excessive brushing with highly abrasive toothpastes can wear down the enamel over time in some cases, as can having overly frequent teeth cleaning sessions at the dental office. The reason for this is that most conventional abrasives used in both prophylaxis paste and some home-use toothpastes tend to have a more jagged morphology and are capable of abrading the teeth.

In order to reduce the tendency of conventional abrasives to scratch the enamel, such abrasives are ground down into extremely fine particles (typically less than 10 microns, and often less than 1 micron) so as to still maintain adequate cleaning ability while reducing their abrasiveness. However, more finely ground abrasives, while excellent at removing stains and other thinly-coated foreign debris on the enamel, are less effective in removing thicker films of soft foreign debris, such as plaque, compared to larger-sized abrasives. Hence, there is a tradeoff between using larger, more abrasive particles for their plaque-cleaning ability and smaller, less abrasive particles more suitable for polishing the teeth and removing stains but which are less effective in removing plaque and other soft foreign debris.

For example, prophylaxis pastes used by dentists during routine teeth cleaning procedures tend to include larger abrasive particles since such teeth cleaning is carried out only infrequently. Thus, some abrasion of the enamel is permitted in order to exploit the better plaque-removal properties of such larger abrasives. On the other hand, toothpastes intended for daily use typically include extremely finely-ground abrasives having a particle size of 1 micron or less in order to minimize abrasion of the enamel. However, because such finely-ground abrasives are not as good as larger particles in their ability to remove plaque, and in light of the tendency of people to brush for only short periods of time, many people do not adequately remove plaque from their teeth during routine brushing. Whereas longer brushing with such toothpastes may remove more plaque, excessive brushing with more abrasive toothpastes can remove enamel over time.

In light of the foregoing, what are needed are improved toothpastes and other dentifrices which included a solid cleaning component that is effective in removing plaque and other soft tooth deposits but which did not significantly abrade tooth enamel.

It would be an additional improvement in the art to provide toothpastes and other dentifrices that had enhanced plaque-removal capabilities such that plaque could be more effectively removed even during shorter brushing routines compared to conventional toothpastes.

Moreover, it would be an improvement in the art to provide dental compositions with enhanced plaque-removal capabilities which, nevertheless, allowed for longer brushing routines without also causing more abrasion of the tooth enamel.

In would yet be an improvement in the art to provide dental compositions which also provided for enhanced cleaning of plaque and other soft debris from soft tissues such as gums and other oral tissues without the irritation of such soft tissues that would inevitably pursue using conventional jagged abrasives of larger size.

Such dental compositions having improved plaque- and other soft debris-removal properties are disclosed and claimed herein.

SUMMARY AND OBJECTS OF THE INVENTION

The present invention relates to improved dental compositions which have enhanced plaque-removal capability compared to conventional toothpastes but which have no greater tendency, or even a decreased tendency, to abrade tooth enamel. Such dental compositions allow for greater plaque removal during a given brushing or other cleaning interval compared to conventional toothpastes. Such compositions achieve such improved plaque- and other soft debris-removal without causing increased removal of tooth enamel like conventional prophylaxis abrasives.

Greater plaque-removal power is accomplished by means of larger, less jagged cleaning particles such as more spherically-shaped particles. Whereas the increased size of such particles greatly assists in loosening and dislodging plaque and other soft debris from tooth surfaces, their more round-edged and less jagged profile greatly reduces their tendency to scratch tooth enamel. The result is the ability to have far greater plaque-removal ability while reducing or eliminating the tendency to scratch enamel during plaque-removal procedures.

The larger, less jagged cleaning particles within the dental compositions of the present invention help to prevent cavities in two ways. First, by removing greater quantities of bacteria-containing plaque, where cariogenic bacteria and their enamel-attacking secretions can fester, the ability of such bacteria and their cariogenic secretions to actually attack the tooth enamel is greatly diminished. Second, by providing greatly increased plaque-removal capability while not increasing, or even reducing, the abrasive action of the toothpaste, more of the protective enamel surface can be preserved over time, thus providing a stronger first line of defense against cariogenic agents of whatever form.

It should be understood that virtually any toothpaste known in the art can be modified to include the more spherical and less jagged cleaning particles of the present invention. Therefore, while the present disclosure discusses certain preferred dental compositions having enhanced plaque-removal properties, it should be understood that any conventional toothpaste known in the art that has been modified so as to incorporate substantial quantities of larger, more spherical cleaning particles is within the scope of the present invention. An example of a toothpaste composition known in the art is set forth in U.S. Pat. No. 3,988,433 to Benedict. There are presently a wide variety of toothpastes in the market sold by companies such as Colgate-Palmolive and Proctor & Gamble. For purposes of disclosing conventional toothpaste compositions, the foregoing patent and known commercial toothpaste compositions are incorporated herein by specific reference.

In order to manufacture a toothpaste having the desired rheological properties, the toothpaste composition will preferably include a carrier, such as a liquid or gel, an appropriate quantity of an abrasive material, and desired medicaments or active ingredients such as fluoride-containing salts. In many cases, toothpastes also include surfactants such as sodium laurel sulfate that cause them to foam when mixing with saliva. This helps to more quickly dissolve the toothpaste in the saliva and increase the uptake of fluorides and other medicaments.

Preferred cleaning particles having a substantially spherical or spheroidal profile within the scope of the invention include, but are not limited to, hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges. It should be appreciated that it is more important for the cleaning particles of the invention to be substantially free of sharp, jagged edges rather than their necessarily being spherical or spheroidal in shape. Thus, any substantially round-edged, non-jagged particle should be understood to be within the scope of the present invention.

In order for the substantially non-jagged cleaning particles of the present invention to be effective in removing plaque and other soft debris from the surface of enamel and the surrounding soft tissues, they will preferably have a particle size in a range from about 10 microns to about 200 microns, more preferably in a range from about 20 microns to about 150 microns, and most preferably in a range from about 30 microns to about 120 microns.

Such round-edged cleaning particles are preferably included in an amount in a range from about 10% to about 90% by volume of the dental composition, more preferably in a range from about 20% to about 80% by volume, and most preferably in a range from about 30% to about 70% by volume. In the event that such round-edged cleaning particles have a density that is similar to the density of the dental composition as a whole, such particles should be included in an amount of at least about 10% by weight of the dental composition, more preferably greater than about 20% weight, and most preferably greater than about 30% by weight.

Round-edged particles can be added to the dental compositions either by themselves or in combination with entrained gas or air bubbles. Unlike more jagged abrasive particles, more spherical or round-edged particles, such as hollow glass spheres, do not render toothpaste foams unstable. Just the opposite—they tend to stabilize foams. In addition, low density fillers such as hollow glass spheres can act to greatly reduce the density of toothpastes, either alone or in combination with entrained gas. Reducing the density of toothpastes is on strategy for delivering a reduced quantity, but not a reduced concentration, of active dental agents such as fluorides.

In light of the foregoing, it is object of the invention to provide toothpastes and other dentifrices which include a solid cleaning component that is more effective in removing plaque and other soft tooth deposits but which does not significantly abrade tooth enamel.

It is an additional object to provide toothpastes and other dentifrices that have enhanced plaque-removal capabilities such that plaque can be more effectively removed even during shorter brushing routines compared to conventional toothpastes.

Moreover, it is an object of the invention to provide dental compositions with enhanced plaque removal capabilities which nevertheless allow for longer brushing routines without also causing more abrasion of the tooth enamel.

In is yet an object and feature of the invention to provide dental compositions which provide for enhanced cleaning of plaque and other soft debris from soft tissues such as gums and other oral tissues without the irritation of such soft tissues that would inevitably pursue using conventional jagged abrasives of larger size.

These and other objects and features of the present invention will become more fully apparent from the following description and appended claims, or may be learned by the practice of the invention as set forth hereinafter.

DETAILED DESCRIPTION OF THE PREFERRED EMBODIMENTS

I. INTRODUCTION

The present invention relates to compositions and methods used in the removal of plaque and other soft debris found on tooth surfaces. The inventive compositions include relatively large-sized cleaning particles which are substantially round edged so as to provide enhanced plaque-cleaning while being substantially nonabrasive on tooth enamel. Such dental compositions allow for greatly enhanced plaque removal during standard brushing regimens compared to conventional toothpastes. The enhanced plaque-cleaning capabilities of the compositions of the present invention allow for greater plaque removal, even during the relatively short brushing times employed by the average person, who generally brushes for 60 seconds or less.

Because conventional abrasives tend to be highly irregular in shape and very jagged, they are typically milled into extremely fine powders in order to reduce their tendency to abrade and remove tooth enamel. Because of this, conventional toothpastes include abrasives that are very finely ground in order to protect the enamel (typically 1 micron or less) while provide some polishing and cleaning properties. On the other hand, larger-sized conventional abrasives, such as those used in typical prophylaxis compositions, can be quite abrasive and are capable of abrading and removing tooth enamel. Fortunately, teeth cleaning is only performed once or twice a year, thus reducing the threat of permanent damage to the enamel.

In comparison to conventional abrasives, the plaque-removal particles of the present invention are far less abrasive since they are selected to be substantially spherical, spheroidal or at least round edged with a minimum of jagged edges, as are typical in most abrasive powders. This allows the inventive plaque-removal particles to be included in far greater size and concentration compared to conventional abrasives without the risk of abrading and damage to the enamel. Because the removal of soft tooth debris such as plaque is more a function of particle size rather than abrasiveness, the larger but less abrasive particles of the present invention have shown a surprising ability to remove plaque and other soft tooth debris while protecting against abrasion of the enamel compared to conventional abrasives The larger, less jagged cleaning particles within the dental compositions of the present invention help to prevent cavities in two ways. First, by removing greater quantities of bacteria-containing plaque, where cariogenic bacteria and their enamel-attacking secretions can fester, the ability of such bacteria and their cariogenic secretions to actually attack the tooth enamel is greatly diminished. Second, by providing greatly increased plaque-removal capability while not increasing, or even reducing, the abrasive action of the toothpaste, more of the protective enamel surface can be preserved over time, thus providing a stronger first line of defense against cariogenic agents of whatever form.

In the case where low density fillers such as hollow glass spheres are used as the round-edged cleaning particle, the inventive compositions can optionally be utilized as a vehicle for delivery a lower quantity, but not a lower concentration, of active dental agents such as fluorides. Fluorides and other medicaments are very useful in preventing tooth decay and treating other dental or oral ailments. The active ingredients in toothpaste and other dentifrices are usually safe when applied topically to tooth surfaces and/or gums. Medications found in toothpastes generally have little or no utility if ingested and can be harmful or even fatal if ingested in great enough quantities. This is particularly true in the case of children, who are generally much more sensitive to toxic doses of fluoride or other medicaments, or medicaments in which the threshold level of toxicity is far less in children due to their greatly smaller size and body weight compared to adults. By way of comparison, an adult weighing six times more than a child would have to ingest roughly six times more of a toxin in order for the toxin to have the same level of harm or toxicity.

Although toothpaste manufactures recommend that children only use a "pea-size" quantity of toothpaste on the brush, such warnings are unheeded by children who either cannot read or do not fully comprehend or appreciate the risks associated with ingesting toothpaste. Moreover, children are often influenced by television and print advertisements showing a generous, full-bodied strip of toothpaste across the entire length of the toothbrush bristles.

II. CONSTITUENTS WITHIN THE INVENTIVE DENTAL COMPOSITIONS

It should be understood that virtually any toothpaste in the market or known in the art can be modified so that it includes substantial quantities of substantially spherical or round-edged cleaning particles in order to improve the plaque-removal capability of such toothpaste. Therefore, while the present application discusses certain preferred methods and/or additives that facilitate the formation of toothpastes having substantially spherical or round-edged cleaning particles, it should be understood that any conventional toothpaste known in the art that incorporates substantial quantities of such cleaning particles will be within the scope of the present invention. An example of toothpaste compositions known in the art is set forth in U.S. Pat. No. 3,988,433 to Benedict, as well as those commonly sold in the market, which have heretofore been incorporated by reference for purposes of disclosure.

A. Base Composition

The portion of the dental composition exclusive of the substantially spherical or round-edged cleaning particles comprises the "base composition". In other words, the "base composition" is that portion of the overall dental composition in addition to the inventive cleaning particles. In the case where the toothpaste includes a low density cleaning particle, such as hollow glass spheres, the base composition will supply most of the mass or weight of the final dental composition. The base composition typically comprises one or more dental agents dispersed within a carrier. In the case of dental compositions used to clean stains and polish teeth, the base composition will preferably include an abrasive or polish.

1. Dental Agents

The primary dental agent found in virtually all toothpastes is fluoride, which is an anticarious compound used to prevent tooth decay. Examples of fluoride compounds useful as a decay prevention agent include, but are not limited to, sodium fluoride, potassium fluoride, calcium fluoride, magnesium fluoride, sodium fluorosilicate, stannous fluoride, stannous monofluorophosphate, sodium monofluorophosphate, and copper fluoride. Each of the foregoing fluoride compounds comprises a "fluoride ion source". A more complete discussion of fluoride compounds useful in fighting cavities may be found in U.S. Pat. No. 3,535,421 to Briner et al. For purposes of disclosure, the foregoing patent is incorporated herein by specific reference.

In order to deliver an effective amount of fluoride to a person's teeth, the foamed dental compositions of the present invention will include a fluoride concentration such that the fluoride ions are included in a range from about 10 ppm to about 3500 ppm, more preferably in a range from about 850 ppm to about 1150 ppm of fluoride ions. The exact amount of fluoride will depend on the solubility and dispersibility of fluoride and also FDA guidelines for fluoride-containing toothpaste. The FDA presently requires toothpastes labeled as "fluoride toothpastes" to include at least 900 ppm of available fluoride ions.

Other dental agents or medicaments that can be included instead of, or in addition to, fluoride include antimicrobial agents that can be added to fight gum and periodontal diseases and desensitizing agents. Examples of antimicrobial agents include, but are not limited to chlorhexidine, tetracycline, cetyl pyridinium chloride, benzalkonium chloride, cetyl pyridinium bromide, methylbenzoate, propylbenzoate, and peroxides. Examples of desensitizing agents include, but are not limited to, potassium nitrate, citric acid, citric acid salts, strontium chloride, and the like.

2. Carrier

In order to deliver the appropriate concentration of dental agent to the user, the dental agent should be dispersed within a flowable substance that will allow for the dental agent to be dispensed onto e.g., a toothbrush. Because any toothpaste or dentifrice known in the art can be modified to include substantial quantities of substantially spherical or round-edged cleaning particles, the appropriate carrier could be any substance known in the art that has been found useful as a carrier in manufacturing conventional toothpaste and tooth gels.

The term "carrier", as used herein, is a broad term defined as one or more components which dilute and deliver the dental agent in appropriate quantities in an appropriate manner. Hence, appropriate carriers may include solid, liquid, gel-like, and gaseous components. Examples of components found in carriers within conventional toothpastes are set forth in U.S. Patent No. 3,988,433 to Benedict, the disclosure of which is incorporated herein by reference. Although Benedict may not necessarily use the term "carrier" to define the components found therein, any component other than the dental agent or medicament found in the composition of Benedict may fairly be referred to as a "carrier" component.

Materials that are used as carriers may also be used for other purposes in a dentifrice composition, such as acting as a humectant, abrasive, thickener, foaming agent, surfactant, and the like. Thus, although one of the components used in a toothpaste may be identified as providing a particular function, as used herein such other components will normally be classified under the rubric of being a "carrier" so long as it in some way aids in the delivery of an appropriate concentration of fluoride or other dental agent.

Carriers typically include a water-soluble gel or other material that gives bulk and the desired flow properties to the dental composition. Typically, a thickener or gelling material is dispersed in water or other solvent such as glycerine or polyethylene glycol to yield a carrier safe for use inside a person's mouth.

In order to protect the teeth and other oral tissues of the user, it will be preferable for the carrier to have a pH in a range from about 5 to about 9, more preferably in a range from about to about 8. Examples of buffers and bases that can be used to adjust the pH include citrate, citrate-bicarbonate, and phosphate buffers, sodium hydroxide and amines.

3. Thickening Agents

A common constituent within a carrier will be a thickening material, which may be used to provide bulk and a suitable consistency. Thickeners may be especially important in the case where the dentifrice compositions are foamed since they may assist in stabilizing the entrained gas. They also may help keep the foamed composition firm and from having a liquid consistency.

Appropriate thickeners may include either inorganic organic thickeners, or both. Inorganic thickeners that may be included in the dentifrice and toothpaste compositions of the present invention include flumed silicas dispersed in water, such as Cab-o-sil available from Cabot Corporation, and thickening silicas, including those available from W. R. Grace designated as Sylox 15.

Appropriate organic thickeners include natural and synthetic gums and colloids. Examples of organic thickeners include carrageenan (derived from Irish moss), xanthan gum, guar gum, other polysaccharide gums, sodium carboxymethyl cellulose, starch, polyvinylpyrrolidone, hydroxyethylpropylcellulose, hydroxybutylmethylcellulose, hydroxypropylmethylcellulose, hydroxyethylcellulose, other cellulosic ethers, and carboxypolymethylene. Such materials are typically dispersed in water and/or other solvents, such as glycerine or polyethylene glycol.

Thickening materials will preferably be incorporated in the compositions of the present invention in a concentration in a range from about 0.05% to about 25% by weight of the composition, and preferably in a range from about 0.1% to about 10% by weight.

4. Abrasives and Polishes

The carrier will typically include one or more abrasive materials to help clean and polish the teeth. Because solids are inexpensive and can add bulk, they will normally comprise a substantial fraction of the carrier. Almost any granular solid or powder can act as an abrasive or polish, although certain solids are preferred in order to clean, yet avoid scratching, the tooth enamel. Conventional abrasives typically include salts having anti-tartar activity and which include, but are not limited to, dicalcium orthophosphate, calcium carbonate, silica and silicates, beta-phase calcium pyrophosphate, sodium metaphosphate, long chain polyphosphates such as sodium hexametaphosphate and cyclic phosphates such as sodium trimetaphosphate as well as alkylmetatripolyphosphates such as sodium tripolyphosphate and potassium tripolyphosphate.

Because the abrasives and polishes, if included at all, will be used in combination with the larger-sized cleaning particles of the invention, they will be included in lessor quantities than if used alone. The term "abrasive" includes polishes, which are generally very fine abrasives. Thus, the concentration of conventional abrasives and polishes will preferably be in a range from about 0.5% to about 60% by weight of the dentifrice, and more preferably in a range from about 10% to about 30% by weight of the dentifrice. The abrasive and polish components should be distinguished from the larger and substantially spherical or round-edged cleaning particles used for enhanced plaque removal. Thus, the term "abrasive" shall be construed to constitute an abrasive component other than larger and substantially spherical or round-edged cleaning particles even though such cleaning particles may themselves import some level of abrasive activity.

Polishing agents may be included in dentifrice compositions that contain siliceous materials, such as silica, which have a mean particle size up to about 10 microns and a very high surface area, e.g. in the range of 150–750 square meters/gram. Polishing agents differ from abrasives mainly in the former having a smaller particle size. A preferred polishing agent is a precipitated amorphous hydrated silica, such as Sorbosil AC-35 marketed by Crosfield Chemicals. Other polishing agents may also be employed, including peroxide reactive polishing agents such as sodium bicarbonate, calcium carbonate, as well as sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina, and bentonite.

When polishing agents are present in the dentifrice composition of the present invention, they are preferably included in a range from about 1% to about 30% by weight of the dental composition, more preferably in a range from about 5% to about 20% by weight.

5. Foaming and Stabilizing Agents

In the case where a foamed toothpaste is desired, foaming and stabilizing agents may be included. As used in the present invention, the term "foaming agent" is defined as any substance that aids, or otherwise helps, the dentifrice composition become foamed or be maintained in a foamed state. Foaming agents generally work in conjunction with mechanical foaming devices, such as high speed mixing devices.

In order for pre-foamed dentifrice compositions to have a commercially practical shelf-life, the foamed compositions need to be shelf stable as a foam for prolonged periods of time and subsequently be ready for application. Stabilized foaming agents within the scope of the present invention should be non-toxic and should not contribute to the formation of carries. There are many foaming and stabilizing agents known that are capable of safely and effectively stabilizing foamed dentifrice compositions including, but are not limited to, soaps, proteins, extract of licorice root, fatty acids, and sulfite liquids.

6. Surfactants

Surfactants may be included in order to aid in dispersing the dentifrice composition throughout the oral cavity and also as a cleansing agent. They also may act as a foaming agent as discussed above. Surfactants help disperse the toothpaste within water and saliva found in the mouth during brushing. Surfactants may also improve the cosmetic acceptability and foaming properties of the dentifrice in the oral cavity.

Among the organic surfactants useful in the practice of the present invention are salts of the higher alkyl sulfates, such as sodium lauryl sulfate (SLS) or suitable alkyl sulfates having 8 to 18 carbon atoms in the alkyl group; sodium lauryl sulfoacetate, salts of sulfonated monoglycerides of higher fatty acids, such as sodium coconut monoglyceride, sulfonate or other suitable sulfonated monoglycerides of fatty acids of 10 to 18 carbons; salts of amides of high fatty acids, e.g., 12 to 16 carbon atoms, with lower aliphatic amino acids, such as sodium-N-methyl-N-palmitoyl taurides sodium N-lauroyl-, N-myristoyl- and N-palmitoyl sarcosinates; salts of esters of fatty acids with isothionic acid or with glycerol monosulfate, such as the sodium salt of monosulfated monoglyceride of hydrogenated coconut oil fatty acids; salts of olefin sulfonates, e.g., alkene sulfonates or hydroxyalkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt is typically sodium, potassium or mono-, di- or triethanolamine.

Mixtures of two or more surfactants can be used if desired to obtain desired properties. Additional useful surfactants may include the non-ionic, cationic, zwitterionic, amphoteric non-soap organic synthetic detergents. A full range of suitable surfactants is disclosed in U.S. Pat. No. 3,988,433 issued to Benedict, the disclosure of which has been incorporated herein by reference.

Surfactants are preferably included in the dentifrice of the present invention is at a concentration in a range from about 0.5% to about 3% by weight, and more preferably from about 1% to about 2% by weight.

7. Humectants

It may be desirable to include a humectant material in a dentifrice or toothpaste composition in order to maintain moisture in the composition and keep the composition from becoming excessively stiff or hardened. Suitable humectants include, but are not limited to glycerin, sorbitol, and other polyhydric alcohols that are suitable for human consumption. The humectant may be included in an amount up to about 40% by weight of the dentifrice composition. Alternatively, the dentifrice composition may contain up to about 40% by weight of a paraffin oil as a non-humectant softening agent.

8. Miscellaneous Components

Various other miscellaneous materials and components may be incorporated into the dentifrice composition of the present invention. Non-limiting examples of these various components include solid lightweight fillers, polishing agents, peroxides, colorants, dyes, flavoring and sweeteners.

Bicarbonate compounds, when included in the dentifrice components of the present invention as a cleansing or refreshening agent, are present at a concentration in a range from about 5% to about 20% by weight, and preferably in a range from about 8% to about 15% by weight. The particle size of the bicarbonate compounds can range from about 10 to about 300 microns. A particle size of about 20–60 microns is preferred, although the smaller particle size bicarbonate compounds can be more readily dispersed in the dentifrice carrier.

Peroxide compounds may be used as an ingredient in the dentifrice and toothpaste compositions of the present invention as a cleansing or whitening agent. When peroxide compounds are present in the dentifrice composition, the peroxide compounds are preferably included in a range from about 0.25% to about 5% by weight of the dentifrice composition, more preferably in a range from about 0.5% to about 2.0% by weight. Peroxide compounds suitable for use with the dentifrice and toothpaste compositions of the present invention include metal peroxides such as calcium peroxide, magnesium peroxide, and zinc peroxide.

Colorants such as pigments and dyes may be used in the practice of the present invention. Pigments include non-toxic, water insoluble inorganic pigments such as titanium dioxide and chromium oxide greens, ultramarine blues and pinks and ferric oxides, as well as water insoluble dye lakes prepared by extending calcium or aluminum salts of FD&C dyes on alumina such as FD&C Green #1 lake, FD&C Blue #2 lake, FD&C #30 lake and FD&C # Yellow 15 lake. The pigments have a particle size in a range of about 0.1–500 microns, preferably about 0.1–50 microns, and are preferably included in a concentration of about 0.5% to about 3% by weight.

Dyes used in the practice of the present invention are generally food color additives presently certified under the Food Drug and Cosmetic Act for use in food and ingested drugs, including dyes such as FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphthol-6-monosulfonate), FD&C Green No. 3 (disodium salt of 4-{4-(N-ethyl-p-sulfobenzylamino)-phenyl]-(4-hydroxy-2-sulfoniumphenyl) methylene}-[1-(N-ethyl-N-p-sulfobenzyl)-δ-3, 5-cyclohexadienimine], FD&C Blue No. 1 (disodium salt of dibenzyldiethyldiaminotriphenylcarbinol trisulfonic acid anhydride), FD&C Blue No. 2 (sodium salt of disulfonic acid of indigotin) and mixtures thereof in various proportions. The preferred concentration of dye for the most effective result, when dyes are used in the present invention, is in an amount in a range from about 0.05% to about 10% by weight of the dentifrice compositions, and preferably from about 0.5% to about 2% of the total weight of the dentifrice composition.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon, lemon, orange, and methyl salicylate. Suitable sweetening agents include sucrose, lactose, maltose, sorbitol, sodium cyclamate, perillartine, and sodium saccharin. Suitable flavor and sweetening agents may together comprise from about 0.01% to about 5% of the dentifrice compositions.

Various other materials may be incorporated into the dentifrice composition of this invention. Non-limiting examples thereof include preservatives, silicones and chlorophyll compounds, antibacterial agents such as chlorhexidine, halogenated diphenyl ethers such as Triclosan, desensitizing agents such as potassium nitrate and potassium citrate and mixtures thereof. These adjuvants are incorporated in the dentifrice composition in amounts which do not substantially adversely affect the properties and characteristics desired, and are selected and used in proper amounts, depending upon the particular type of dentifrice component involved.

B. Low Abrasion Cleaning particles

The terms "low abrasion cleaning particles", "substantially spherical particles" and "round-edged particles" shall refer to particles in accordance with the invention which differ from conventional abrasives in that they are substantially rounded and have a minimum of jagged edges. Jagged or sharp edges are capable of abrading and scratching the enamel. Smoothing or eliminating such sharp or jagged edges greatly reduces the tendency of the resulting particles from scratching or abrading tooth enamel.

Reducing or eliminating the tendency of such particles to scratch or abrade tooth enamel allows for the use of far greater-sized particles compared to conventional abrasives without the danger of greater damage to the enamel. In fact, the opposite is true—using larger-sized cleaning particles which are substantially spherical or round-edged instead of conventional abrasives of whatever size generally reduces the tendency to scratch or abrade the enamel. On the other hand, since it has been found that there is a direct correlation between particle size and the ability to loosen and remove plaque and other soft tooth debris, the use of the low abrasion cleaning particles yields dental compositions of greatly enhanced plaque-removal ability and low abrasion.

Preferred cleaning particles having a substantially spherical or spheroidal profile within the scope of the invention include, but are not limited to, hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, non-jagged edges.

It should be appreciated that it is more important for the cleaning particles of the invention to be substantially free of sharp, jagged edges rather than their necessarily being spherical or spheroidal in shape. Thus, any substantially round-edged, non-jagged particle should be understood to be within the scope of the present invention.

A presently preferred hollow glass bubble or sphere useful in forming dental compositions according to the present invention is available from 3M and sold as K1 series Scotchlite Glass Bubbles. These glass bubbles are made from soda-lime-borosilicate glass, have a target crush strength (90% survival) of 250 psi, and have a true density of 0.125 g/cc. The bubble size ranges from about 20 to about 120 microns, with the 50th percentile of size distribution being 65 microns.

In terms of particle size, such hollow glass bubbles are substantially larger than conventional abrasives used in toothpastes. Because conventional abrasives are generally quite jagged and abrasive, they are milled to much smaller sizes (usually less than 10 microns) in order to reduce their tendency to abrade teeth. Surprisingly, the much larger sized glass bubbles (e.g., 20–150 microns in diameter), while providing little if any abrasive power for cleaning stains from enamel due to their spherical shape and larger size, have been found to be particularly effective in removing plaque from teeth and soft tissues such as gums. Thus, toothpastes that include significant quantities of hollow glass spheres, or any type of large, spheroidal or otherwise round-edged filler, will provide enhanced plaque-removal capability while being generally less abrasive to enamel compared to conventional abrasives and polishes found in toothpastes.

Other hollow glass bubbles having varying compositions, crush strengths, densities and particle size distributions would also provide the aforementioned plaque-cleaning properties. In fact, virtually any round-edged, non-jagged particle would be less abrasive, although those having a relatively-large diameter (i.e., from about 10 to 200 microns) will be particularly effective in cleaning plaque from teeth and soft tissues.

In order for the substantially non-jagged cleaning particles of the present invention to be effective in removing plaque and other soft debris from the surface of enamel and the surrounding soft tissues, they will preferably have a particle size in a range from about 10 microns to about 200 microns, more preferably in a range from about 20 microns to about 150 microns, and most preferably in a range from about 30 microns to about 120 microns.

Such round-edged cleaning particles are preferably included in an amount in a range from about 10% to about 90% by volume of the dental composition, more preferably in a range from about 20% to about 80% by volume, and most preferably in a range from about 30% to about 70% by volume. In the event that such round-edged cleaning particles have a density that is similar to the density of the dental composition as a whole, such particles should be included in an amount of at least about 10% by weight of the dental composition, more preferably greater than about 20% weight, and most preferably greater than about 30% by weight.

C. Density Reduction Components.

In the case where the cleaning particle comprises a low density solid filler, such as hollow glass spheres, such cleaning particles will also comprise a "density reduction component" since dental compositions formed therewith will have substantially reduced density. Low density cleaning particles can be included either alone or in combination with entrained gas bubbles, which can further reduce the density of the dental composition. Reducing the density allows for the delivery of reduced quantities, but not reduced concentrations, of active dental agents such as fluorides. Low density dental compositions made thereby are especially suitable for use a children's toothpastes since they have enhanced plaque-removal properties while reducing the amount of fluoride or other active dental agents that may be ingested.

Unlike more jagged abrasive particles, more spherical or round-edged particles, such as hollow glass spheres, do not render toothpaste foams unstable. Just the opposite—they tend to stabilize foams. Thus, replacing conventional abrasives, in whole or in part, with more spherical shaped cleaning particles increases the ability to entrain significant quantities of gas if desired to yield low density dental compositions.

It should be understood that reducing the density is the same as increasing the volume and bulk per unit weight. In this way, the volume of the dental composition can be significantly or greatly increased by the density reducing means in order to allow a larger volume of the dental composition to be introduced onto a toothbrush, while reducing the actual amount of fluoride and other active ingredients actually delivered into a person's mouth.

In the case where it is desired for the spherical cleaning particles to significantly reduce the density of the resulting dental composition, the solid lightweight filler will preferably have a density or specific gravity that is less than about 0.5 $g/cm^3$, more preferably less than about 0.3 $g/cm^3$, and most preferably less than about 0.1 $g/cm^3$.

Nonporous fillers such as hollow glass spheres are preferred due to their impermeability to liquids and gels. Porous low density fillers such as expanded perlite, vermiculite and other expanded geological materials should be treated with a sealer in order to prevent their absorption of liquid or gel carrier components. Otherwise, they would quickly lose their density-reduction properties.

In the case where it is desired to provide an expanded dental composition of substantially reduced density, the density reduction component is preferably included in an amount in a range from about 25% to about 90% by volume, more preferably greater than about 30% by volume, and most preferably greater than about 50% by volume.

III. PREPARATION OF THE INVENTIVE DENTAL COMPOSITIONS

The inventive dentifrice and toothpaste compositions incorporating relatively large-sized, round-edged cleaning particles can be prepared using conventional techniques known in the art. For example, the dentifrice or toothpaste compositions can be prepared by blending the solid ingredients with a liquid carrier, i.e., polyalkylene glycol, which is normally viscous at room temperature. Conventional adjuvants can then be included. The dental compositions according to the present invention preferably have a rheology so as to be capable of being expressed from an appropriate storage container, such as a squeeze tube or syringe.

Once the desired dentifrice or toothpaste composition is formed, the composition can be optionally foamed to form a low density dentifrice or toothpaste. Foam is produced in dentifrice or toothpaste compositions by introducing air or a gas into the toothpaste or dentifrice composition. This can be done by either mechanical or chemical means. Alternatively, gas can be incorporated into the dental composition, which is then stored in compressed form under pressure. Upon dispensing the composition, the compressed gas will develop foam within the toothpaste upon being exposed to atmospheric pressure.

In one embodiment, the dentifrice composition is foamed prior to packaging (referred to as pre-foamed). When the dentifrice composition is foamed and then packaged, the dentifrice composition preferably comprises a foam stabilizing agent so that the foamed dentifrice composition is shelf-stable for a commercially practical period of time. The dentifrice composition is preferably foamed using mechanical means, such as high speed mixing or other agitation. The foamed composition is then placed into a suitable container, such as a conventional toothpaste tube or pump container for storage. The inventive compositions should be stable as a foam: i) after mixing; ii) after storage of the composition for extended periods of time; and iii) after delivering a portion of the foamed composition from the container onto a toothbrush.

In another embodiment of the present invention, chemical foaming agents are used to foam the dentifrice composition prior to packaging. Chemical foaming agents create foam or entrained gas when the foaming chemicals are mixed together. An example of chemical foaming is the formation of carbon dioxide from the chemical reaction of aluminum sulfate and sodium bicarbonate. As with mechanical foaming, a foam stabilizer is preferably included with the chemically foamed dentifrice compositions in order to stabilize the foamed composition during storage, use and reuse.

In still another embodiment, the dentifrice composition may constitute a pressurized foaming composition. As used in the present invention, the term "pressurized foaming composition" is defined as a suspension of compressed gas voids within a liquid. A common example of a pressurized foaming composition is conventional shaving cream, wherein a gas is compressed in a container and upon release, a foamed material is produced. In connection with the present invention, the dentifrice composition is formed using conventional methods as discussed above. The dentifrice composition is then placed in a container with a suitable compressed gas, under pressure, using conventional compression techniques known in the art. Subsequently, when the dentifrice composition is dispensed from the container, the pressure of the gas causes the dentifrice composition to be dispensed as a foamed dentifrice composition. An example of a suitable propellant and foaming agent is carbon dioxide gas.

Alternatively, the dentifrices can be placed into a container under pressure along with foaming agents that will cause the dentifrice to foam upon being dispensed from the container and being exposed to the atmosphere. Similarly, a container of toothpaste can be provided in conjunction with a separate compartment of compressed gas, which gas is caused to mix with, and cause foaming of, the toothpaste during dispensing.

In yet another embodiment, air can be entrained into the initially unfoamed dental composition by means of the pumping action required to express the dental composition from the container within which it is stored.

Finally, some or all of the entrained air can be replaced with an appropriate low density, lightweight filler such as hollow glass spheres, hollow ceramic spheres, hollow and other low density plastic spheres, expanded geologic materials such as perlite which have been sealed to prevent substantial absorption of liquids, and the like. These fillers are typically blended with the other components using low shear mixing in order to avoid breaking such fillers. Air and other gases can be entrained along with the lightweight fillers according to any appropriate method set forth above.

IV. EXAMPLES OF THE PREFERRED EMBODIMENTS

The following examples are presented in order to more specifically teach the preferred compositions and methods for forming and using the plaque-removal dental compositions according to the present invention. The examples which have actually been made are written in past tense, while those that are merely hypothetical are written in present tense. Although some examples are hypothetical in nature, they are based on or derived from actual mix designs and conditions for making plaque-removal dental compositions according to the present invention.

EXAMPLE 1

A base dental composition of normal density that was suitable for use in brushing or cleaning teeth was made by combining the following components:

| | |
|---|---|
| Distilled water | 21.6% |
| Glycerin | 25% |
| Sorbitol | 25.26% |
| Sodium Fluoride | 0.25% |
| Sodium Benzoate | 0.22% |
| Fumed Silica | 3% |
| Abrasive Silica | 19.5% |
| Aspartame | 0.22% |
| Surfactants | 2.6% |
| Xanthan gum | 0.46% |
| Carbomer | 0.3% |
| Flavors | 1.0% |
| FD & C Colorants | 0.59% |

The base dental composition had a density of 1.4 g/cm$^3$. Thereafter, the base dental composition was "spiked" with various quantities of hollow glass spheres in order to study the effect of adding a lightweight filler on the density of the resulting dental composition. The hollow glass spheres that were added were K1 series Scotchlite Glass Bubbles manufactured by 3M. These hollow glass spheres were made from soda-lime-borosilicate glass, had a target crush strength (90% survival) of 250 psi, and had a density of 0.125 g/cm$^3$. The size distribution of the hollow glass spheres ranged from about 20 to about 120 microns, with the 50th percentile of size distribution being 65 microns.

To 100 parts of the base composition were added the following quantities of K1 series Scotchlite Glass Bubbles, measured in terms of parts and percent by volume, to form various "filled compositions". The resulting densities of the filled compositions are also listed:

| Quantity Added | Volume Percent | Resulting Density |
|---|---|---|
| 0 parts | 0% | 1.4 g/cm$^3$ |
| 30 parts | 15% | 0.96 g/cm$^3$ |
| 50 parts | 25% | 0.93 g/cm$^3$ |
| 70 parts | 35% | 0.86 g/cm$^3$ |
| 100 parts | 50% | 0.81 g/cm$^3$ |

The above values were plotted and found to be essentially linear, meaning that there is an essentially linear relationship between the volume of added hollow glass spheres and the reduction in density within this concentration range. This is because of the tremendous disparity between the density of the base composition and that of the hollow glass spheres. Of course, since the hollow glass spheres do, in fact, add some additional weight to the dental composition, the relationship is not precisely linear, particularly at very high concentrations of hollow glass spheres (i.e. approaching 100% by volume).

The resulting filled dental compositions had a substantial reduction in density, which means that hollow glass spheres worked well in creating expanded, low density dental compositions that had greatly reduced mass per unit volume but which did not have substantially reduced concentrations of fluoride or other active ingredients.

The dental compositions having hollow glass spheres were tested to determine how well they cleaned teeth. Whereas the reduced density toothpastes were found to provide the same level of benefit with regard to the effects of fluoride treatment of teeth compared to conventional toothpastes, a surprising and unexpected benefit was increased plaque removal without any detectable increase in the abrasion of tooth enamel. It is believed that the increased size of the hollow glass spheres resulted in an enhanced ability of the dental composition to mechanically break up and disperse the plaque, thereby facilitating the dissolution and removal of plaque from the teeth and surrounding soft tissues by the solvents and surfactants present within the dental compositions. The rounded, non-jagged profile of the hollow glass spheres allowed for the aforementioned plaque removal without significant scratching of the enamel or irritation of the surrounding gums or gingival tissue.

EXAMPLE 2

Dental compositions suitable for use in brushing or cleaning teeth are made from a base composition having the following components, exclusive of the substantially spherical cleaning particles, expressed as a percentage by weight of the base composition exclusive of the substantially spherical cleaning particles:

| | |
|---|---|
| Distilled water | 30% |
| Glycerin | 25% |
| Flavor and color | 1.5% |
| Mannitol | 15% |
| Sodium laurel sulfate | 2% |
| Xanthan gum | 1% |
| Abrasive silicon dioxide | 25% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 3

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| | |
|---|---|
| Distilled Water | 20% |
| Propylene glycol | 35% |
| Flavor and color | 1.5% |
| Sorbitol | 15% |
| Potassium laurate | 1% |
| Polysorbate 60 | 1% |
| Carbomer 974 NF | 1% |
| Abrasive aluminum oxide | 25% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 4

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| | |
|---|---|
| Distilled Water | 20% |
| Propylene glycol | 20% |
| Polyethylene glycol 300 | 15% |
| Flavor and color | 1.5% |
| Xylitol | 15% |
| Octaoxyethlylene glycol monododecyl ether | 1% |
| Polysorbate 20 | 1% |
| Pemulen TR-1 NF | 2% |
| Abrasive aluminum oxide | 25% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 5

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| | |
|---|---|
| Glycerin | 31% |
| Polyethylene glycol 300 | 35% |
| Flavor and color | 1.5% |
| Sodium saccharin | 1% |
| Potassium laurate | 1% |
| Polyalkylene oxide modified polydimethyl siloxanes | 1% |
| Sodium oleate | 2% |
| Fumed Silicon dioxide | 2% |
| Abrasive calcium fluorosilicate | 25% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 6

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| | |
|---|---|
| Distilled Water | 63% |
| Flavor and color | 1.5% |
| Phenylalanine | 1% |
| Sodium decane sulfonate | 1% |
| Carbomer 934 | 6% |
| Abrasive aluminum oxide | 27% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 7

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| | |
|---|---|
| Distilled Water | 22% |
| Propylene glycol | 36% |
| Flavor and color | 1.5% |
| Mannose | 15% |
| Tetradecyltrimethyl ammonium bromide | 1% |
| Sodium di-2-ethylhexyl sulfosuccinate | 1% |
| Locust bean gum | 1% |
| Abrasive titanium dioxide | 22% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 8

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| Propylene glycol | 57% |
| --- | --- |
| Flavor and color | 1.5% |
| Fructose | 15% |
| Carbomer 910 | 4% |
| Abrasive mica | 22% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 9

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| Distilled Water | 20% |
| --- | --- |
| Polyethylene glycol | 35% |
| Flavor and color | 1.5% |
| Sorbitol | 15% |
| Abrasive silicon dioxide | 20% |
| Mica | 8% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 10

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| Distilled Water | 20% |
| --- | --- |
| Glycerin | 50% |
| Flavor and color | 1.5% |
| Sucralose | 1% |
| Sodium deoxycholate | 2% |
| Abrasive aluminum oxide | 25% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 11

Dental compositions suitable for use in brushing or cleaning teeth are made from a base composition having the following components, exclusive of substantially spherical cleaning particles, expressed as a percentage by weight of the base composition exclusive of the substantially spherical cleaning particles:

| Distilled Water | 23% |
| --- | --- |
| Polyethylene glycol | 38% |
| Flavor and color | 1.5% |
| Sorbitol | 15% |
| Abrasive silicon dioxide | 22% |
| Fluoride source and preservative | 0.5% |

The dental compositions made according to this example include substantially spherical cleaning particles dispersed throughout the base composition in various amounts. The final dental compositions include various quantities of the substantially spherical cleaning particles in a concentration in a range from about 10–90% by volume in 5% increments. The substantially spherical cleaning particles have a particle size in a range from about 10 microns to about 200 microns in diameter. Increasing the concentration of substantially spherical cleaning particles is found to increase the plaque-removal power of the dental compositions.

The substantially spherical cleaning particles include at least on of the following: hollow glass spheres, hollow aluminum oxide spheres, hollow ceramic spheres, hollow plastic spheres, polystyrene beads, polystyrene foam beads, polypropylene spheres, polyethylene spheres, polymeric beads, hollow plastic spheres, cork, glass beads, ceramic beads, metallic balls, and previously jagged minerals and other particles that have been milled, agglomerated, coated or otherwise treated so as to have substantially rounded, nonjagged edges In the case where some or all of the substantially spherical cleaning particles comprises a low density filler, such as hollow glass, hollow ceramic, or hollow plastic spheres, polystyrene foam beads, or cork, the resulting dental compositions will also have greatly reduced density. In order to maintain the mandated concentration of fluoride, some additional fluoride may need to be added depending on the density and concentration of the substantially spherical cleaning particles being added to form the inventive dental compositions.

EXAMPLE 12

The density of any conventional toothpaste is reduced by adding one or more low density, lightweight fillers having a density less than 0.5 g/cc (preferably less than 0.3 g/cc, most preferably less than 0.1 g/cc) in order to reduce the density of the original toothpaste by 10–90% in increments of 5% selected from the following: hollow glass spheres (e.g., made from silica, soda-lime-borosilicate, aluminum oxide, silica-alumina ceramic, or alkali-alumino-silicate ceramic), hollow ceramic spheres, expanded perlite (treated with a sealer), expanded vermiculite (water resistant), aerogels (treated to be water resistant), expanded silica gels, cork, polystyrene foam particles, polyethylene particles, polypropylene particles, and hollow plastic spheres.

To the extent that the foregoing low density, lightweight fillers are substantially spherical, or at least substantially round-edged, and have a particle size in a range from about 10 microns to about 200 microns in diameter, the resulting low density dental compositions also have increased plaque-removal capability.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental composition having enhanced plaque-removal capability consisting essentially of:
   a carrier selected from the group consisting of liquids, gels, pastes, and mixtures thereof;
   a fluoride ion source that provides from about 10 ppm to about 3500 ppm of fluoride ions;
   at least about 10% by volume of substantially spherical plaque-cleaning particles having a particle size in a range from about 20 microns to about 150 microns in diameter, at least a portion of which maintain their particle size during plaque removal; and
   an abrasive solid, separate from the substantially spherical plaque-cleaning particles, having a substantially irregular and nonspherical morphology and a particle size of less than about 10 microns and included in a concentration of less than about 30% by weight of the dental composition.

2. A dental composition having enhanced plaque-removal capability comprising:
   a carrier selected from the group consisting of liquids, gels, pastes, and mixtures thereof;
   a fluoride ion source that provides from about 10 ppm to about 3500 ppm of fluoride ions; and
   at least about 10% by volume of at least one of hollow aluminum oxide, ceramic, or glass bubbles having a particle size in a range from about 10 microns to about 200 microns in diameter.

3. A dental composition as defined in claim 1, wherein the substantially spherical plaque-cleaning particles are included in an amount in a range from about 10% to about 90% by volume of the dental composition.

4. A dental composition as defined in claim 1, wherein the substantially spherical plaque-cleaning particles are included in an amount in a range from about 30% to about 70% by volume of the dental composition.

5. A dental composition as defined in claim 1, wherein the optional nonspherical abrasive has a particle size of less than about 1 micron.

6. A dental composition as defined in claim 1, wherein the substantially spherical plaque-cleaning particles comprise hollow glass bubbles.

7. A dental composition as defined in claim 1, wherein the substantially spherical plaque-cleaning particles have a density less than about 0.5 g/cm$^3$.

8. A dental composition as defined in claim 1, wherein the substantially spherical plaque-cleaning particles have a density less than about 0.1 g/cm$^3$.

9. A dental composition as defined in claim 1, further including an antimicrobial agent.

10. A dental composition as defined in claim 1, wherein the dental composition has a rheology such that it may be expressed onto a toothbrush using a squeeze tube.

11. A dental composition as defined in claim 1, wherein the substantially spherical plaque-cleaning particles are included in an amount in a range from about 20% to about 80% by volume of the dental composition and have a particle size in a range from about 30 microns to about 120 microns in diameter.

12. A dental composition as defined in claim 2, wherein the dental composition has a rheology such that it may be expressed onto a toothbrush using a squeeze tube.

13. A dental composition as defined in claim 2, further including an abrasive solid having a substantially irregular and nonspherical morphology and a particle size of less than about 10 microns.

* * * * *

UNITED STATES PATENT AND TRADEMARK OFFICE
CERTIFICATE OF CORRECTION

PATENT NO. : 6,083,489
DATED : July 4, 2000
INVENTOR(S) : Dan E. Fischer; Steven D. Jensen It is certified that error appears in the above-identified patent and that said Letters Patent are hereby corrected as shown below:

Col. 1, ln. 62: after "relied" change "up" to --upon--

Col. 4, ln. 6: before "edges" change "nonjagged" to --non-jagged--

Col. 4, ln. 44: after "it is" and before "object" insert --an--

Col. 4, ln. 58: before "is yet" change "In" to --It--

Col. 5, ln. 25: after "while" change "provide" to --provides--

Col. 7, ln. 64: after "about" and before "to" insert --6--

Col. 8, ln. 12: after "include" change "flumed" to --fumed--

Col. 8, ln. 50: after "in" change "lessor" to --lesser--

Col. 9, ln. 59: after "palmitoyl" change "taurides" to --laurides--

Col. 10, ln. 12: after "invention" and before "at" delete [is]

Col. 10, ln. 61: after "FD &C" change "# Yellow" to --Yellow #--

Col. 13, ln. 16: after "for use" and before "a" insert --in--

Col. 17, ln. 9: after "least" change "on" to --one--

Col. 17, ln. 59: after "least" change "on" to --one--

UNITED STATES PATENT AND TRADEMARK OFFICE
CERTIFICATE OF CORRECTION

PATENT NO. : 6,083,489
DATED : July 4, 2000
INVENTOR(S) : Dan E. Fischer; Steven D. Jensen It is certified that error appears in the above-identified patent and that said Letters Patent are hereby corrected as shown below:

Col. 18, ln. 44: after "least" change "on" to --one--

Col. 19, ln. 29: after "least" change "on" to --one--

Col. 20, ln. 11: after "least" change "on" to --one--

Col. 20, ln. 62: after "least" change "on" to --one--

Col. 21, ln. 44: after "least" change "on" to --one--

Col. 22, ln. 26: after "least" change "on" to --one--

Col. 23, ln. 8: after "least" change "on" to --one--

Col. 23, ln. 57: after "least" change "on" to --one--

Signed and Sealed this

Eighth Day of May, 2001

Attest:

NICHOLAS P. GODICI

Attesting Officer

Acting Director of the United States Patent and Trademark Office